United States Patent [19]
Lenck

[11] Patent Number: 4,701,161
[45] Date of Patent: Oct. 20, 1987

[54] METHOD AND APPARATUS FOR INSEMINATION IN VIVO AND IN VITRO

[76] Inventor: Lucien-Charles Lenck, 34, Rue Marechal de Lattre de Tassigny, 63000 Clermont Ferrand, France

[21] Appl. No.: 854,883

[22] Filed: Apr. 23, 1986

[30] Foreign Application Priority Data

Apr. 24, 1985 [FR] France .............................. 85 06516

[51] Int. Cl.⁴ ........................ A61F 2/04; A61M 25/00
[52] U.S. Cl. ..................................... 604/55; 128/1 R
[58] Field of Search .................. 128/1 R; 604/55, 51, 604/93

[56] References Cited

U.S. PATENT DOCUMENTS 4,574,000  3/1986  Hunter .............................. 128/1 R Primary Examiner—C. Fred Rosenbaum
Assistant Examiner—Sherri E. Vinyard
Attorney, Agent, or Firm—Michael Ebert

[57] ABSTRACT

A method for effecting in vitro/in vivo fertilization in which an oocyte and its follicle are removed from the mother. In a host mother, the wall which separates the intraperitoneal fluid from the extraperitoneal fluid is perforated, and placed within this perforation is a culture container. Introduced into this container are the oocyte and its follicular fluid, the spermatozoa and a culture medium. After fertilization and multiplication of the cells under optional artificial conditions, the transfer of the embryo and the nidation are carried out in a substantially normal manner.

11 Claims, 5 Drawing Figures

METHOD AND APPARATUS FOR INSEMINATION IN VIVO AND IN VITRO

BACKGROUND OF INVENTION

1. Field of Invention

The present invention relates generally to medical techniques directed toward remedying certain cases of sterility, particularly in humans, and more particularly to an apparatus facilitating artificial fertilization.

2. Status of Prior Art

By artificial fertilization is meant the technique which permits fertilization of the ovum or oocyte by the spermatozoon under conditions other than those provided by nature, for instance, under so-called "in vitro" conditions. An in-vitro fertilization technique entails the removal of the ovum follicle by means of a celioscope or echograph, allowing it to fertilize after capturing the spermatozoa, then allowing it to multiply in a physiological medium for a period close to 48 hours, and finally injecting the embryo thus formed into the uterus of the host mother, awaiting its implantation or nidation.

The above-described in-vitro operating steps are performed in a laboratory under conditions which are as close as possible to those of the natural medium of fertilization; that is to say, the peritoneal cavity.

This prior art method, although having the advantage of remedying certain cases of sterility, nevertheless has a rather limited rate of success, in the order of 10 to 25%. This low percentage of reliability appears to be due primarily to the difficulty of carrying out the last step; that is to say, the reimplanting of the fertilized egg or embryo. One of the reasons for this difficulty might be because of the closing of the neck of the uterus through which the egg implanatation cannula must be introduced three days after ovulation. This period of time results from the cumulative times of fertilization and multiplication in vitro. The penetration of the neck of the uterus which is closed during this post-ovulatory period, is frequently hermorrhagic, and it is known that blood is a factor which is unfavorable for the implanting of the egg.

There are other reasons that might explain the low rate of reliability. It is known that normally there is a negative pressure of a few millimeters of mercury as compared with atmospheric pressure in the peritoneal cavity. This reduction in pressure is normally transmitted into the uterine cavity through the fallopian tubes which are normally permeable. Numerous cases of sterility are due precisely to the closing of those tubes. In the above-mentioned method of in-vitro fertilization, the injection of liquid into the uterus would tend to produce an increase in pressure, and this could interfere with good contact between the egg and the mucous coat of the uterus.

Certain sterilities treated by in-vitro fertilization occur, however, despite permeable tubes. The above-noted interplay of pressures could then explain finding the embryo in a growth phase in the tubes. The egg in this case would have been aspirated under the effect of the positiveintra-uterine pressures towards the negative intra-abdominal or peritoneal pressures.

SUMMARY OF INVENTION

A method of fertilization in accordance with the invention has the objectives of effecting the required transfer without having to force the uterine passage and therefore avoiding hemorrhage, of allowing peritoneal reduction in pressure to act in the uterine cavity or even favoring it, and of requiring only simple means for carrying it out.

A method in accordance with the invention which is designated as "in-vitro/in-vivo" fertilization consists essentially in removing an oocyte in its follicle from the mother, perforating a wall in the host mother that separates the intraperitoneal fluid from the extraperitoneal fluid, placing a culture container in the wall perforation, and introducing the oocyte and its follicular liquid, the spermatozoa and a culture medium into this container whereby after fertilization and multiplication of the cells under optimal artificial conditions, the transfer of the embryo and the nidation can take place in a substantially natural manner.

It appears already, upon examination of this method, that the introduction of the egg into the culture container which may be hemorrhagic upon the passage through the neck of the uterus, precedes by a period of more than at least three days the transfer of the embryo into the uterine cavity, and that this transfer is effected under conditions closer to the natural conditions, which are those involving the transfer from the ovary through the tubes to the uterine cavity.

The method according to the invention is optimally carried out by means of an apparatus serving as receptacle which constitutes the culture container, this receptacle being formed in characteristic manner by a rather rigid neck of a length substantially equal to the thickness of the uterine wall. This neck is provided, at least on its outside, with a relief intended to avoid the sliding of the neck along the perforation of the wall, and by a part known as the balloon, which constitutes the container proper. The relief is preferably a simple circumferential relief arranged in a plane substantially perpendicular to the axis of the neck.

In accordance with another principal characteristic of the invention, the part known as the balloon is formed of a flexible material. This last-mentioned characteristic makes it possible, among other things, to transmit the peritoneal pressure reduction into the uterine cavity.

The materials constituting the neck and the balloon are rather rigid in the case of the former and flexible in the case of the latter. It is advantageous to have both elastic. Thus, the material of the neck is preferably a silicone elastomer of maximum hardness, while the constituent material of the balloon is a silicone elastomer of rather slight hardness but great elasticity.

The end of the neck away from the balloon is furthermore shaped as a sectored collar, each sector advantageously having a folding groove. The purpose of the collar is to avoid, at least during the estimated time of transfer, the closing of the orifice of the receptacle by the development of a mucous coat on the uterus.

In accordance with a preferred embodiment of the invention, the shape of the neck is that of the surface of two coaxial ellipsoidal segments or barrels, the junction portion of the segments forming said relief in intaglio. Due to this arrangement, the muscle constituting the peritoneal wall can find firm support in the intaglio relief, while the inner wall of the neck which has a corresponding protruding relief favors the retention of a provisional plugging member, as will be explained hereinafter.

Finally, a so-called guide strand is preferably attached within the neck in such a manner that the attachment can be broken by means of twisting movements exerted on the strand.

OUTLINE OF DRAWING

The present invention will be better understood and details with regard to it will become evident from the description which will be given both of the method and the apparatus, with reference to the figures of the drawing attached hereto, wherein.

DESCRIPTION OF INVENTION

Figure 1:
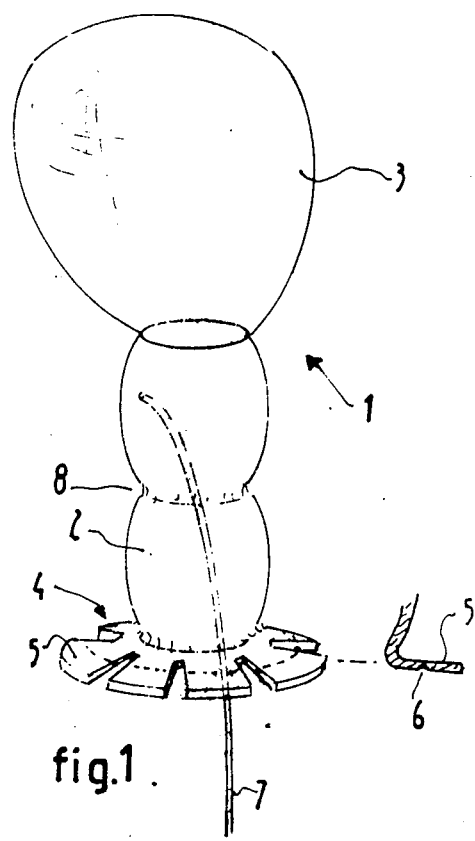
FIG. 1 is a perspective illustration in an enlarged scale of a container which makes it possible to carry out the method of the invention.

In FIG. 1, a device 1 in accordance with the invention has the general structure of a receptacle formed from a neck 2 and a balloon-like container 3, which is approximately spherical. The constituent material of the wall of balloon 3 is a silicone elastomer, which is preferred over other elastomers such as natural rubber, polyester elastomers, etc., in view of the permeability of silicone to carbon dioxide and in view of the inert chemical nature of this material.

Neck 2 is made of a material which is preferably still elastic but more rigid than the constituent material of the balloon. The constituent material of the neck can, for instance, be a silicone elastomer of rather great hardness (70° Shore). The structure of the neck may furthermore be a composite, for instance, one formed of a tubular enforcement of identical shape of polycarbonate, lined on the inside and outside with silicone elastomer.

The end of neck 2 opposite the end joined to balloon 3 is provided with a collar 4. This collar is formed preferably of a plurality of sectors such as 5 which are slightly spaced apart from each other, each sector having a folding groove 6 on its lower face. The usefulness of the sector groove configuration is that it permits a folding action to facilitate the positioning of the device by means of tubulures, as will be described further below.

Referring still to FIG. 1, it can be noted that a guide strand 7 is connected to the inner face of the neck. This connection or attachment is sufficiently fragile, so that it can be broken by twisting the strand. The attachment is advantageously effected by cementing the end of the strand by means of a silicone elastomer. The usefulness of the guide strand will also be described further below.

Still referring to FIG. 1, there can furthermore be noted the shape of the neck in the form of superimposed barrels (coaxial ellipsoidal segments). The length of the neck is in the order of 15 to 20 MM; that is to say, slightly greater than the bottom wall, called the uterine wall, of the uterine cavity. Thus, due to the intaglio relief 8 located at the junction of the ellipsoidal segments, the uterine muscle can act on the neck of the device.

Figure 2:
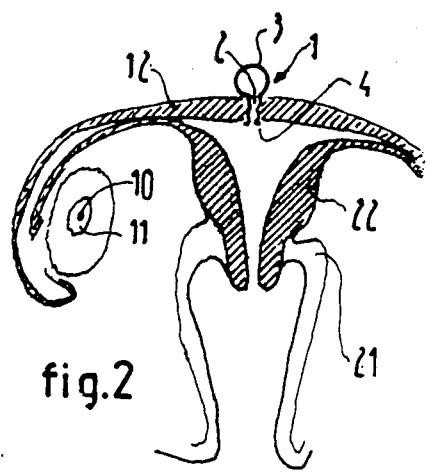
FIG. 2 is a conventional illustration in horizontal section through the genital organs in which an apparatus in accordance with FIG. 1 has been implanted.

In FIG. 2, it will be seen that an apparatus such as that of FIG. 1 has been placed within a perforation in the uterine wall 12 opposite the neck of the uterus. Collar 4 is then located in the uterine cavity while balloon 3 is contained within the peritoneal cavity. This operation can precede the period of ovulation by a certain period of time. Upon ovulation, an oocyte 10 is removed together with its follicular liquid 11 and is then placed by means of a suitable tube into the balloon into which a physiological medium has been previously introduced. The introduction of the ovum is followed immediately by an injection of spermatozoons by means of a similar probe. The fertilization can then take place and nidation occurs within the following days, definitely after the cessation of any possible hemorrhaging.

Figure 3:
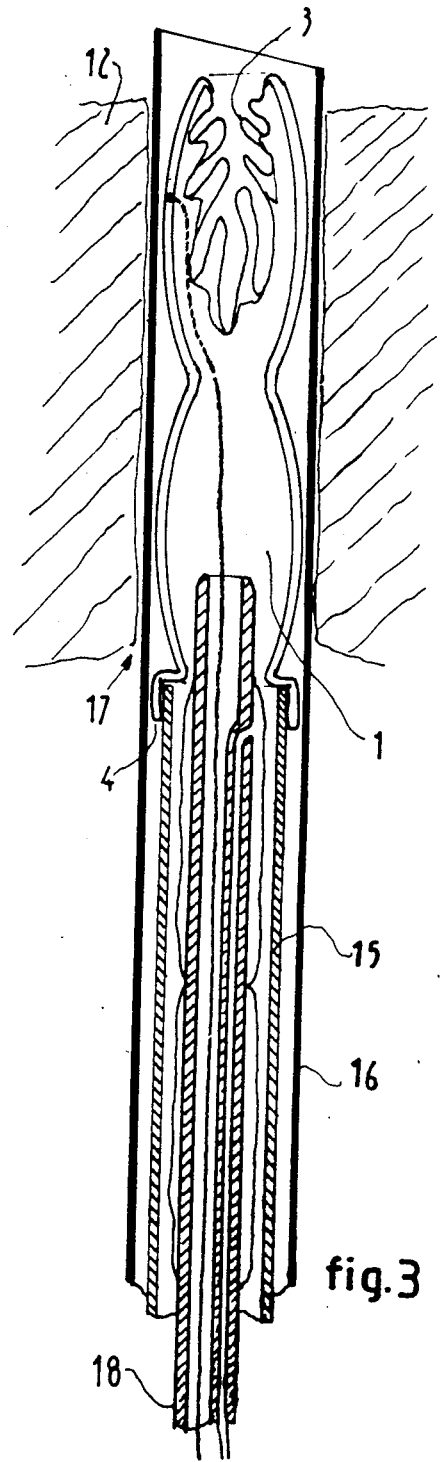
FIG. 3 is an illustrative section through the means for implanting the device of the preceding figures.

FIG. 3 shows an implantation instrument of the invention, and a method of procedure will now be described with reference to this figure. After lining up with the uterine bottom by means of the so-called outer tubulure 16, the uterine wall 12 is perforated at 17 by means of a trocar which is withdrawn after perforating the wall. An internal tubulure 15 surmounted by the device 1, as appears from the figure, is then introduced into the outer tube until device 1 is positioned within the thickness of the perforation. Tubulure 16 is then withdrawn. The relationship between collar 4 of device 1 and the mucous coat of the uterus is then adjusted by manipulating tubulure 16. At the end of this operation, the internal tubulure is then withdrawn.

The distal end of a valve tube 18 (such as a Foley or Tremann catheter) is then introduced into the neck of the device, guiding it on the guide strand 7 which has been previously threaded into the lumen of the tube. When the end of the tube comes against the point of attachment of the strand, the latter is detached from device 1 by twisting it on itself. The position of the valve catheter can then be readjusted in the device. The small balloon of the valve catheter is then inflated so as to create a closed space, the filling of which will permit the expulsion of the balloon 3 out of the neck 2 of the device and its expansion into the peritoneal cavity. The container which can receive the medium and the fertilization elements will have thus been created.

It is also contemplated that the lower end of neck 2 be provided with a flap, for instance a thin sheet of elastomer, in order to avoid rising of the embryo into the balloon during the course of nidation.

Figure 4:
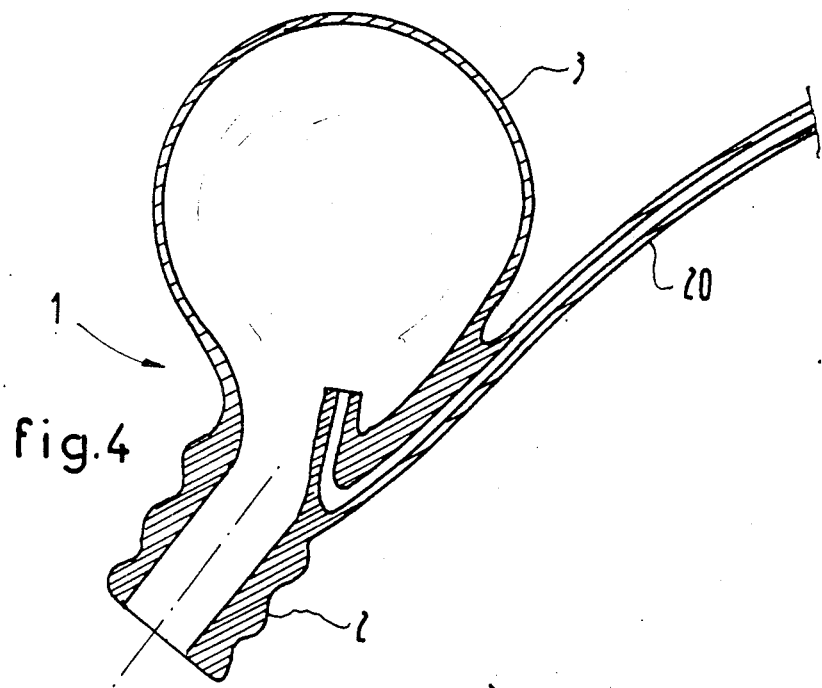
FIG. 4 shows another embodiment of the container in accordance with the invention.

In FIG. 4, a container or receptacle similar to that of FIG. 1 is shown. It differs, however, by the presence of a flexible external tube 20 communicating with balloon 3 in the vicinity of neck 2. The portion of tube 20 which is close to neck 2 preferably has a rigidity close to that of neck 2.

Figure 5:
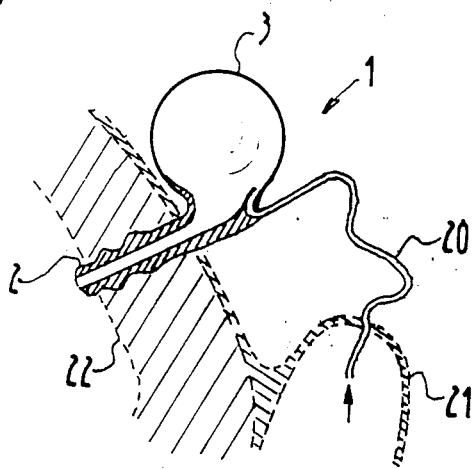
FIG. 5 illustrates an implantation of the container of the preceding figure in the host mother.

In FIG. 5, a container similar to that of FIG. 4 is implanted in the uterine wall 22 in the vicinity of Douglas' cul-de-sac, while tube 20 passes through a perforation in the vaginal wall 21. Tube 20 permits the introduction into the container either of the gametes (ovum, spermatozoa) or of culture medium or of agents intended for the modification of the latter.

Although embodiments of apparatus in accordance with the present invention have been described and shown, it is to be understood that the scope of the invention is not limited thereto, but extends to all devices having the general features enumerated above.

I claim:

1. A device for carrying out in-vitro/in-vivo fertilization in a procedure in which a passage is perforated through the uterine wall in a host mother, said device comprising a balloon-like culture container for receiving an oocyte and its follicular liquid removed from a mother, spermatozoa and a culture medium, and a relatively rigid neck attached to said container and communicating therewith, said neck being insertable in said passage and having a length substantially equal to the thickness of the wall, said neck being provided on its outside with means serving to resist sliding of the neck along said passage.

2. A device as set forth in claim 1, characterized by the fact that the wall of the balloon-like container is formed of a flexible material.

3. A device as set forth in claim 2, characterized by the fact that the constituent materials of the neck and the balloon like container are elastic.

4. A device as set forth in claim 3, characterized by the fact that the end of the neck facing away from the balloon is shaped as a collar.

5. A device as set forth in claim 4, characterized by the fact that said collar is formed by sectors.

6. A device as set forth in claim 5, characterized by the fact that each sector has a folding groove.

7. A device as set forth in claim 6, characterized by the fact that the shape of the neck is that of two coaxial barrel-like segments, the junction of the segments forming an intaglio relief.

8. A device as set forth in claim 7, characterized by the fact that the constituent material of the neck is a silicone elastomer of maximum hardness while the constituent material of the balloon is a silicone elastomer of rather low hardness but great elasticity.

9. A device as set forth in claim 1, characterized by the fact that a guide strand is attached within the neck in such a manner that the attachment can be broken by means of twisting movements exerted on the strand.

10. A device as set forth in claim 1, characterized by the fact that the lower end of the neck is provided with a membrane acting as a flap.

11. An "in-vitro/in-vivo" fertilization method comprising the steps of:
   A removing from a mother an oocyte and the liquid in its follicle;
   B perforating the uterine wall separating intraperitoneal fluid from extraperitoneal fluid in a host mother to form a passage through the wall;
   C placing a culture container having a neck attached thereto and communicating therewith so that the neck extends into the passage through said wall; and
   D introducing the oocyte and its follicular liquid, spermatozoa and a culture medium into said container whereby after fertilization and multiplication of the cells in the container under optimal artificial conditions, the transfer of the embryo from the container through the neck and its nidation can be effected in a substantially natural manner.

* * * * *